United States Patent [19]

Hourani et al.

[11] Patent Number: 4,735,087
[45] Date of Patent: Apr. 5, 1988

[54] IN SITU PAPERMACHINE WEB SOUND VELOCITY TEST

[75] Inventors: Michel J. Hourani, Columbia, Md.; Anders L. Wigsten, Covington, Va.

[73] Assignee: Westvaco Corporation, New York, N.Y.

[21] Appl. No.: 4,653

[22] Filed: Jan. 20, 1987

[51] Int. Cl.[4] .................................... G01N 29/00
[52] U.S. Cl. .............................. 73/597; 73/639; 73/159; 310/336
[58] Field of Search .................. 73/159, 597, 639; 310/326

[56] References Cited

U.S. PATENT DOCUMENTS

| | | | |
|---|---|---|---|
| 3,678,737 | 7/1972 | Miller | 73/639 X |
| 3,683,681 | 8/1972 | Taylor | 73/159 X |
| 4,098,132 | 7/1978 | Mikesell | 73/639 |
| 4,291,577 | 7/1987 | Baum et al. | 73/159 X |

OTHER PUBLICATIONS

"On-Line Measurement of Paper-Mechanical Properties", Baum et al., Tappi/Jul. 1980, vol. 63, No. 7, pp. 63-66.
J. K. Craver and D. L. Taylor, "Nondestructive Sonic Measurement of Paper Elasticity," Tappi, vol. 48, No. 3, Mar., 1965, p. 142.
E. P. Papadakis, "Ultrasonic Methods for Modulus Measurement in Paper," Tappi, vol. 56, No. 2, Feb., 1973, p. 74.
G. A. Baum and L. R. Bornhoeft, "Estimating Poisson Ratios in Paper Using Ultrasonic Techniques," Tappi, vol. 62, No. 5, May, 1979, p. 87.
R. W. Mann, G. A. Baum, and C. C. Habeger, "Elastic Wave Propagation in Paper," Tappi, vol. 62, No. 8, Aug., 1979, p. 115.
R. W. Mann, G. A. Baum and C. C.Habeger, "Determination of All Nine Orthotropic Elastic Constants for Machine-Made Paper," Tappi, vol. 63, No. 2, Feb,. 1980, p. 163.
G. A. Baum, D. C. Brennan, and C. C. Habeger, "Orthotropic Elastic Constants of Paper," Tappi, vol. 64, No. 8, Aug., 1981, p. 97.
G. A. Baum, "Procedures for Measuring the In-Plane Orthotropic Elastic Constants of Paper Using Ultrasonic Techniques," The Institute of Paper Chemistry, Appleton, Wis. IPC Technical Paper Series, No. 119, Dec., 1981.

*Primary Examiner*—Daniel M. Yasich
*Attorney, Agent, or Firm*—W. A. Marcontell; R. L. Schmalz

[57] ABSTRACT

An on-line instrument in rolling contact with a papermachine web determines the web's strength and elastic modulus properties by intermittently pulsed sonic waves transmitted through the traveling web mass between a full circle, piezoelectric transducer emitter and identical receiving transducers respectively displaced from the emitter along the MD and CD web axes. Transducer signals from the receivers are analyzed by cross-correlation function techniques relative to the original stimulation reference signal to isolate the desired data signal from integral noise.

5 Claims, 7 Drawing Sheets

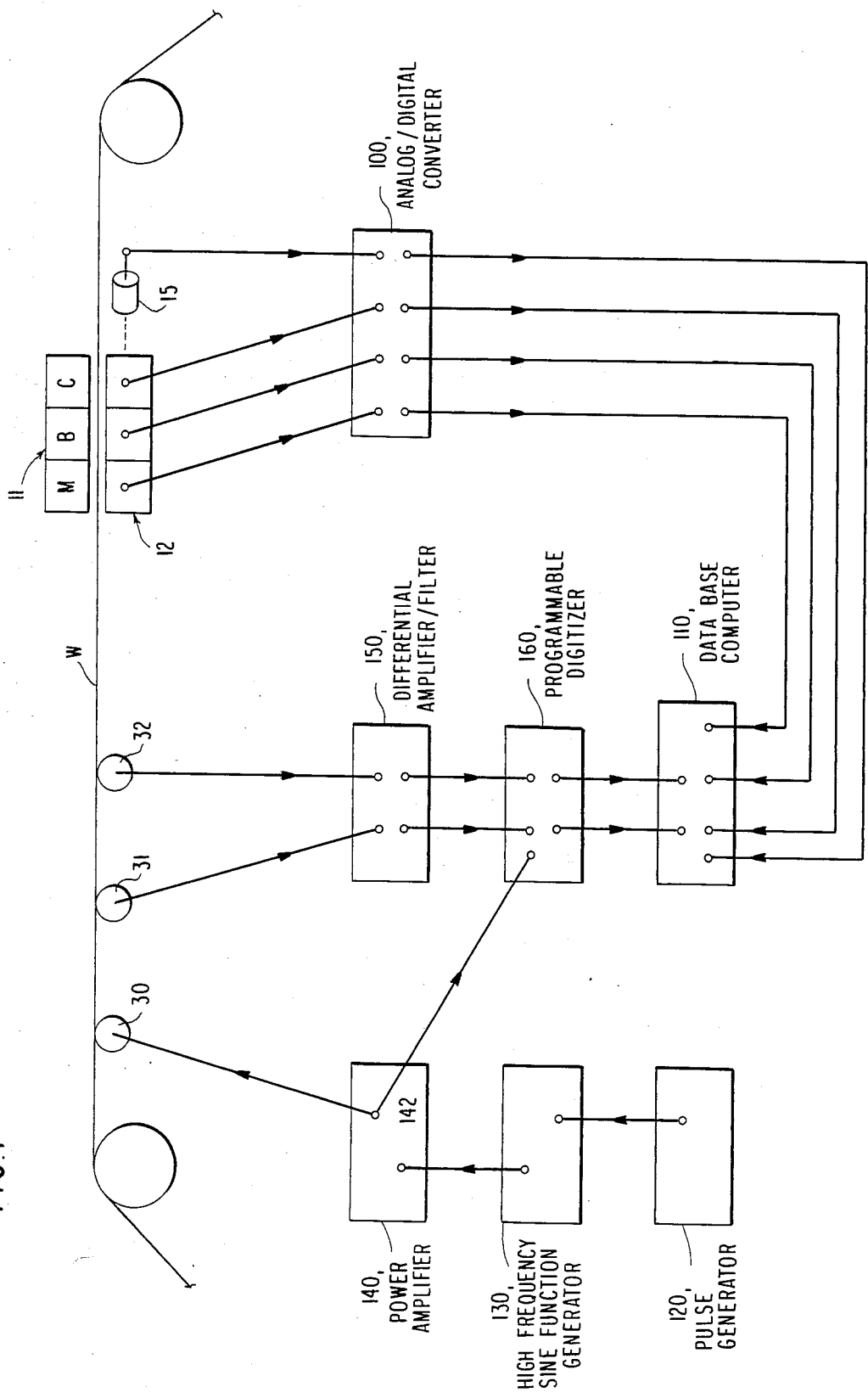

FIG. 11

|  | $\underline{s}$ | | $\underline{m}$ | | |
|---|---|---|---|---|---|
| $t_0$ | $V_0^s$ | X | $V_0^m$ | = | $p_{t_0}^0$ |
| $t_1$ | $V_1^s$ | X | $V_1^m$ | = | $p_{t_0}^1$ |
| $t_2$ | $V_2^s$ | X | $V_2^m$ | = | $p_{t_0}^2$ |
| $t_3$ | $V_3^s$ | X | $V_3^m$ | = | $p_{t_0}^3$ |
| 0 | 0 | | 0 | | |
| $t_x$ | $V_x^s$ | X | $V_x^m$ | = | $p_{t_0}^x$ |
| | | | | | $\overline{\Sigma p_{t_0}^{0 \rightarrow x}}$ |

FIG. 12

|  | $\underline{s}$ | | $\underline{m}$ | | |
|---|---|---|---|---|---|
| $t_0$ | $V_0^s$ | X | $V_1^m$ | = | $p_{t_1}^0$ |
| $t_1$ | $V_1^s$ | X | $V_2^m$ | = | $p_{t_1}^1$ |
| $t_2$ | $V_2^s$ | X | $V_3^m$ | = | $p_{t_1}^2$ |
| $t_3$ | $V_3^s$ | X | $V_4^m$ | = | $p_{t_1}^3$ |
| 0 | 0 | | 0 | | |
| $t_{x-1}$ | $V_{x-1}^s$ | X | $V_x^m$ | = | $p_{t_1}^{x-1}$ |
| $t_x$ | $V_x^s$ | X | $V_0^m$ | = | $p_{t_1}^x$ |
| | | | | | $\overline{\Sigma p_{t_1}^{0 \rightarrow x}}$ |

FIG. 13

|  | $\underline{s}$ | | $\underline{m}$ | | |
|---|---|---|---|---|---|
| $t_0$ | $V_0^s$ | X | $V_2^m$ | = | $p_{t_2}^0$ |
| $t_1$ | $V_1^s$ | X | $V_3^m$ | = | $p_{t_2}^1$ |
| $t_2$ | $V_2^s$ | X | $V_4^m$ | = | $p_{t_2}^2$ |
| $t_3$ | $V_3^s$ | X | $V_5^m$ | = | $p_{t_2}^3$ |
| 0 | 0 | | 0 | | |
| $t_{x-2}$ | $V_{x-2}^s$ | X | $V_x^m$ | = | $p_{t_2}^{x-2}$ |
| $t_{x-1}$ | $V_{x-1}^s$ | X | $V_0^m$ | = | $p_{t_2}^{x-1}$ |
| $t_x$ | $V_x^s$ | X | $V_1^m$ | = | $p_{t_2}^x$ |
| | | | | | $\overline{\Sigma p_{t_2}^{0 \rightarrow x}}$ |

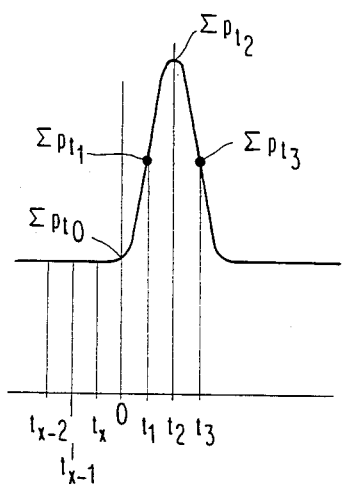

FIG. 14

IN SITU PAPERMACHINE WEB SOUND VELOCITY TEST

BACKGROUND OF THE INVENTION

1. Field of the Invention

The present invention relates to nondestructive testing of paper for mechanical properties. More particularly, the present invention relates an apparatus for continuously testing a paper web ultrasonically while traveling within the papermaking machine.

2. Prior Art

Paper and paperboard strength properties are important to most converting and end-use applications. Mechanical parameters such as ultimate tensile strength, burst, and bending stiffness are the strength indicia of greatest concern to the papermaker.

Tests to ascertain these mechanical characteristics of a given paper web have, traditionally, been destructive of the test sample or specimen. Loss of the sample is of no consequence but the quantity of specialized test equipment, skills and time required to perform the full battery of such tests is enormous when it is considered that a reliable test average requires a large number of test samples.

Over the past decade, nondestructive ultrasonic methods have been developed to measure many of the mechanical properties previously measured by destructive tests. By these methods, a vibration induced sonic disturbance is transmitted through a sample sheet and the resultant wave velocity is measured. Such velocity measurements are taken relative to the test sample fiber orientation, both MD (machine direction) and CD (cross-machine direction), and used to calculate the sheet in-plane elastic parameters of Young's and shear moduli.

As published by Tappi, Vol. 48, No. 3, March, 1965, the technical paper titled "Nondestructive Sonic Measurement of Paper Elasticity" by J. K. Craver and D. L. Taylor thoroughly develops the theoretical relationships between sonic wave velocity and a paper web modulus of elasticity. From the basic theory of Craver and Taylor, a number of authors contributed to the evolution of theory and technology embodied by the report of G. A. Baum and C. C. Habeger concerning "On-line Measurement of Paper Mechanical Properties" appearing in Tappi, Vol. 63, No. 7, July, 1980. U.S. Pat. No. 4,291,577 issued Sept. 29, 1981 to G. A. Baum and C. C. Habeger, discloses the substance of the authors' earlier Tappi report and describes a mechanical system for measuring the sonic wave propagation velocity within a traveling paper web as found within the papermaking machine. Pursuant to the system of Baum and Habeger, three synchronously coordinated idler wheels are positioned in friction drive contact with a moving paper web. Each of the wheels include a single piezoelectric transducer located on the wheel rim for cyclic contact with the traveling web surface. Wheel rotation is mechanically timed so that all three transducers are in simultaneous contact with the paper web. One of the three transducers serves as an ultrasonic signal transmitter whereas the other two are receivers. Relative to the transmitter wheel, one receiver is located at a known distance along the web in the machine direction and the other at the same known distance in the cross-machine direction. When the transducers engage the web, an electrical signal to the transmission transducer stimulates an ultrasonic mechanical vibration which is transmitted through the paper web to the receiver transducers. Responsively, the receivers emit electrical signals for receipt by electronic data process equipment which compares and determines the time interval between original signal emission and signal receipt. This approach to wave velocity measurement has been characterized as the "time-of-flight" technique.

Also applied to paper measurement has been the "wave-phase shift" technique. By the wave-phase shift method, the web contacting wheels are constructed with four quadrant arc piezoelectric transducers for substantially continuous contact with the paper web. A continuously emitted 6.75 kHz sine signal, for example, is electronically processed for phase shift determination. From the phase shift, the wave velocity is derived. The characterization as a "wave-phase shift" measurement technique distinguishes this measurement method from the "time-of-flight" technique.

Both of the prior art wave velocity measurement techniques have respective advantages and disadvantages. The time spans between signal stimulation and receipt are extremely short: in the microsecond range. It is difficult to reliably segregate signal pulses or phase displacements of such short duration from extraneous noise always present in a moving paper web.

Although the "wave-phase shift" signals are continuous and therefore avoid the uncertainties of mechanically timed pulsing intervals, other signal obfuscation mechanisms are operative. For example, each of the piezoelectric transducers are original signal generators of continuous, low amplitude signals over a wide frequency spectrum and relatively high amplitude signals at a natural frequency determined by the momentary web speed driving the transducer wheels. Simultaneously, the transducers respond to sympathetic and harmonic vibrations originating from other sources around the paper machine but not directly related to the machine operation. Even the measurement signal, when received by a reception transducer through a carriage conduit other than a direct route through the web mass, is a noise source due to a greater or less transmission interval depending on the transmission route.

In the midst of all these spurious signal sources, it is essential to instrument reliability that only the original stimulation signal directly transmitted through the web mass is the signal processed for sonic velocity measurement. It is, therefore, a first object of the present invention to teach a process and apparatus for distinguishing these desired, web transmitted, acoustic signals from irrelevant noise signals.

Another object of the present invention is to teach the construction of a novel and acoustically quiet transducer assembly for measuring paper web strength properties.

SUMMARY OF THE INVENTION

These and other objects of the invention are accomplished by a web contacting, sonic transducer wheel assembly in which each of the three, independently rotating, assembly wheels are fabricated with a full and continuous circle, ceramic, piezoelectric annulus that is intimately bedded with an aluminum tire. Each wheel is also mounted within an acoustic isolation housing.

Cooperating with the wheel assembly is an electronic equipment combination which includes a reference/- stimulation signal generator, a programmable digitizer and a computational computer.

One of the transducer wheels is stimulated by the reference signal to emit vibratory disturbances through the web mass. The signal characteristics are a high frequency pulse generated at a low frequency interval i.e. a signal cycle of 50 KH pulse triggered respectively at a 1000 H rate. These disturbances stimulate the other two transducers to emit correspondingly responsive electrical signals. These responsive signals are filtered, integrated, normalized and compared on a time delay sequence for probability comparison to the reference signal by cross-correlation techniques. The specific time delay that provides the greatest probability of synchronization with the reference signal is taken as the "time of flight" sonic transit interval through the web mass.

From such sonic transit interval, the sonic velocity characteristic may be calculated and the signal result combined with independently measured moisture, basis weight and caliper web characteristic signals to determine the strength and elastic modulus characteristics of the web.

BRIEF DESCRIPTION OF THE DRAWINGS

Relative to the drawings wherein like reference characters designate like or similar elements throughout the several figures of the drawings:

FIG. 7 is a signal schematic illustrating the data flow course between the several measuring units of the invention.

FIGS. 11, 12 and 13 are sequentially related cross-correlation data table.

FIG. 14 is a graphic profile of cross-correlation product data.

PREFERRED EMBODIMENT

Figure 1:
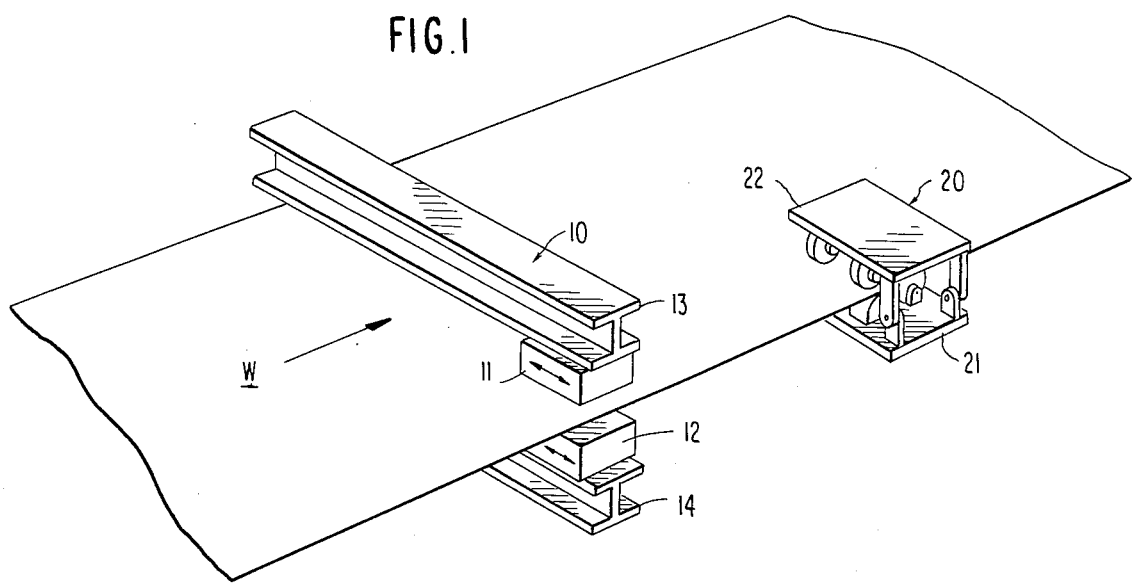
FIG. 1 is a pictorial of the present invention operation environment.
Figure 2:
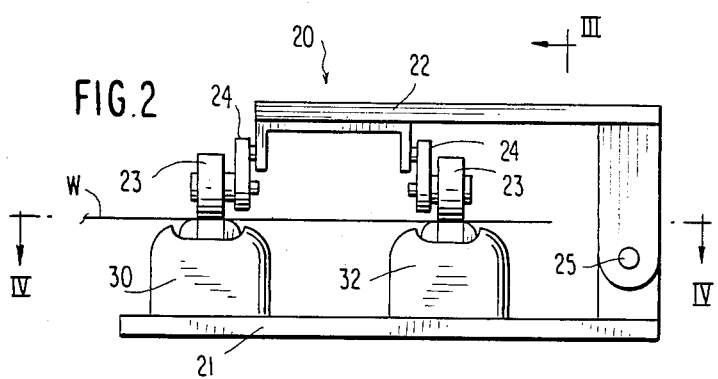
FIGS. 2, 3 and 4 are orthographically related views of the invention transducer wheel unit.
Figure 3:
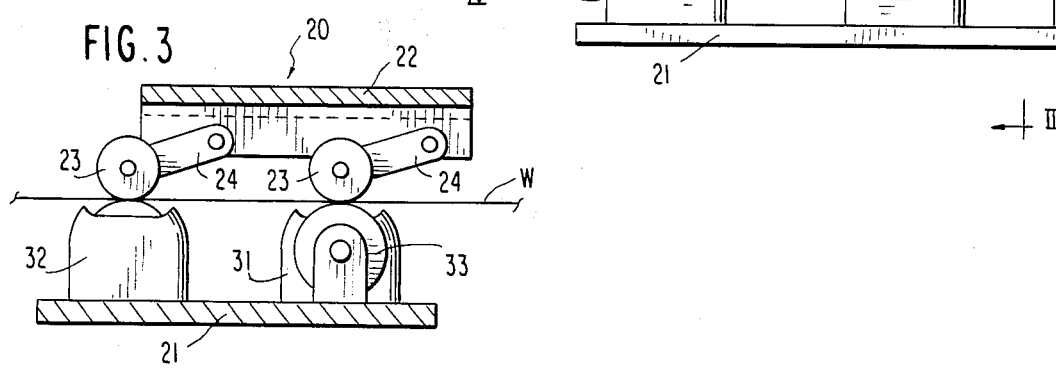
Figure 4:
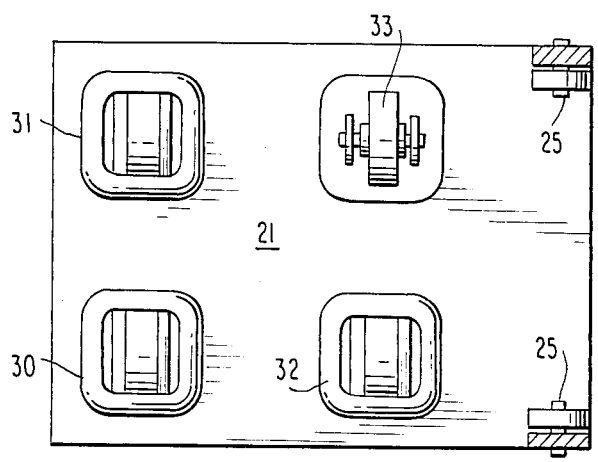

FIG. 1 represents a small portion of dry, papermachine web W in continuous transit through the sensory field of the two instruments utilized by the present invention. The first instrument is a state of the art cross-direction scanner 10 which continuously measures one or more web properties such as moisture, basis weight and caliper by means of emission and reception field sensors disposed in traverse carriages 11 and 12. These carriages reciprocate synchronously across the web width on rigid beams 13 and 14. The reception field sensors transmit electrical signals proportional to the particular web property measured by a respective sensor pair.

Not specifically shown but as an integral portion of the scanning unit 10 is a traverse drive mechanism having a cross-direction position transmitter represented by element 15 on FIG. 7. It is the drive mechanism which moves the traverse carriages 11 and 12 back and forth along the beams 13 and 14 without a structural link therebetween to provide clear passage space for the web between the carriages. The position signal transmitter 15 (FIG. 7) provides the information necessary to correlate a particular web property signal to a specific cross-direction location of the respective sensor on the web. While there are other web monitoring reasons for having a full CD scan of such information, it is only those web properties in CD alignment with the modulus measuring unit 20 that relate to the invention. Position signal transmitter 15 provides the data to make the discrimination.

Further along the web traveling route are disposed those mechanical, web engaging portions of the present modulus measuring instrument 20. This mechanical unit 20 will be described in greater detail relative to FIGS. 2-3, 7 and 8.

As a discrete unit, these mechanical portions of the invention are attached to lower and upper bases 21 and 22, respectively, which are pivotally joined by a pin 25. Preferably, the lower base 21 is secured to the papermachine frame at the edge plane of the web. The specific mounting design is irrelevant except for the characteristics that the entire unit 20 may be detached and removed from the web proximity when necessary. Additionally, the mounting should include a sensitive adjusting mechanism for engaging the unit with the web and, perhaps, for adjusting the parallelism of the unit relative to the web plane.

Upper base 22 secures passive idler wheels 23 rotating about spindles at the free ends of swing arms 24. These idler wheels are geometrically aligned to hold the traveling web in a nip between the idler wheel circumference and the circumference of the transducer wheels below.

It should be noted that the upper base and wheels are pivotally connected to the lower base to minimize the possibility of web damage during installation and for convenience during web threading. At these times, the upper base 22 is rotated 90° away from the web plane.

To the lower base 21 are attached three active transducer wheels 30, 31 and 32 and one passive idler wheel 33. None of the lower base wheels are rotatively connected: each rotates independently of the others. The idler wheel 33 usefulness is limited to that of force balancing: to equalize coupling forces in the web plane due to rotational resistance imposed by the three active wheels.

Figure 6:
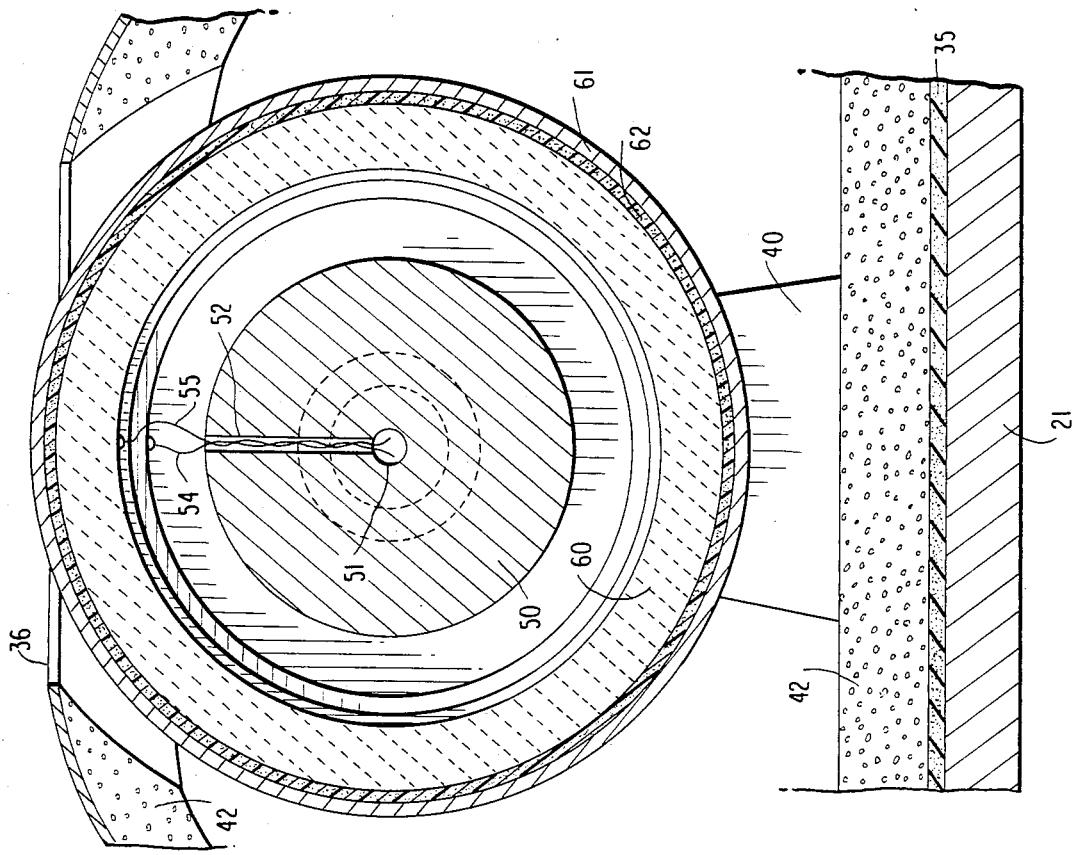
FIGS. 5 and 6 are partial sectional views of a transducer wheel assembly.
Figure 5:
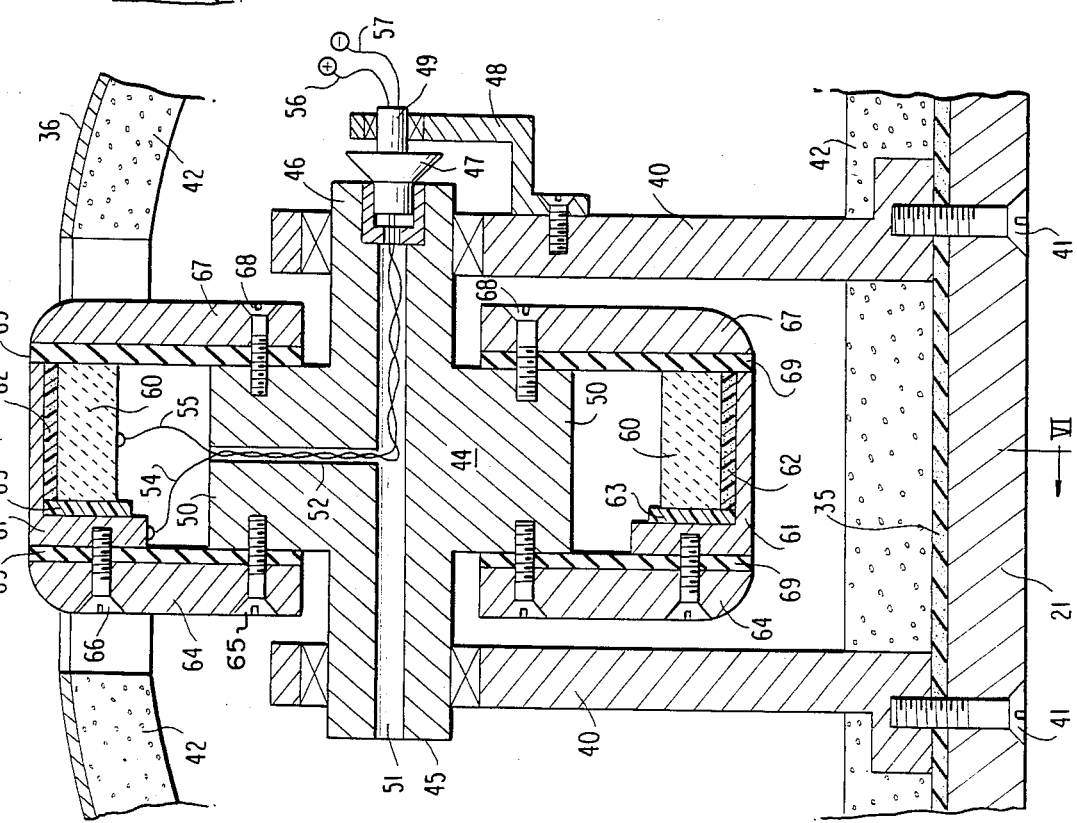
Figure 8:
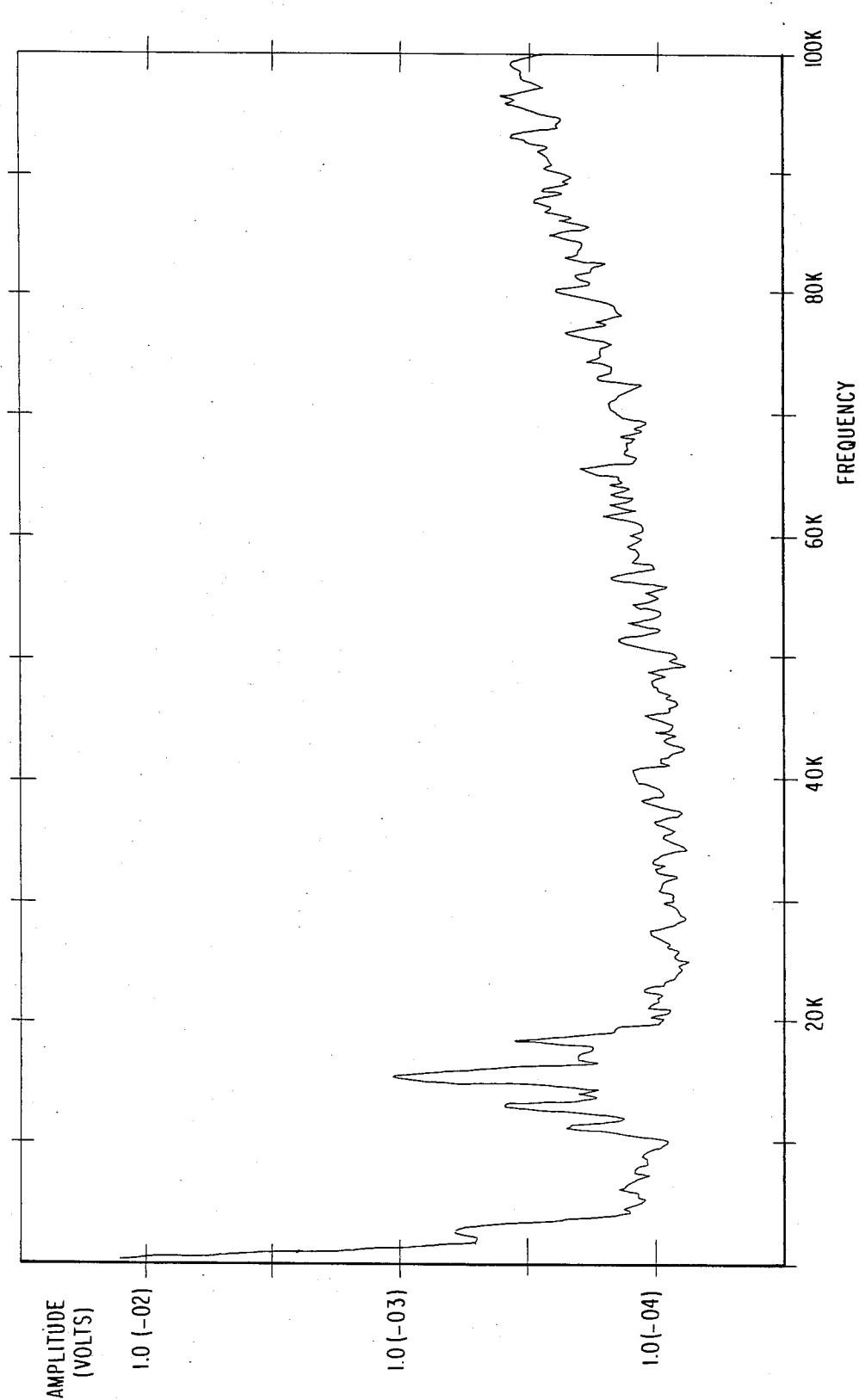
FIG. 8 is a passive noise signal graph of a receiving transducer.

Internal construction of the three transducer wheels, is identical. This construction is shown in detail by FIGS. 5 and 6. However, transducer 30 is electrically connected as an acoustic transmitter whereas transducers 31 and 32 are acoustic receivers. These relationships will be further described relative to the signal schematic of FIG. 7.

Noting some overall characteristics of the transducer wheels, it will first be observed that maximum effort is made to acoustically isolate each transducer unit. To this end, vibration dampening material 35 such as soft rubber is layered between the lower base plate 21 and the footing surfaces of bearing posts 40. Nylon machine screws 41 are used to secure the bearing posts 40 to the lower base plate 21. An outer shell 36 of soft aluminum is used to enclose each transducer unit. Internally, each transducer enclosure is provided with acoustic insulation 42.

Each transducer wheel assembly is constructed about a flanged axle 44 having opposed bearing pins 45 and 46. Concentric with the rotational axis, a mercury slip-ring 47 is provided on the end of bearing pin 46. A bracket appendage 48 from bearing post 40 supports and stabilizes the stationary element 49 of the slip ring 47.

A central bore 51 is provided concentrically through the axle 44 to accommodate the rotating signal conductor leads 54 and 55. These signal leads are drawn from the axle bore 51 through a radial bore 52 in the flange 50.

A continuous, piezoelectric ceramic ring 60 is the primary active element of each transducer wheel. This ring 60 is integrally bedded with a flanged aluminum tire 61 by means of an electrically conductive epoxy compound 62. In assembly, the ceramic ring edge is electrically insulated from the adjacent radial flange of tire 61 by a layer of electrically non-conductive epoxy compound 63.

Independent radial structural links positionally secure the active tire and ring elements concentrically to the axle structure. Such links comprise a disc-shaped aluminum rim 64 secured to the axle flange 50 and the tire flange by nylon machine screws 65 and 66, respectively. However, a sheet 69 of electrical and acoustic insulating material is clamped between the rim 64, the flange 50 and the tire 61 to sonically isolate the tire from the rim.

A similar rim 67, secured to the opposite face of axle flange 50 by nylon machine screws 68, completes the wheel enclosure. As on the first wheel side, a sheet of electrical and acoustic insulating material 69 separates and therefore sonically isolates the rim 67 from the flange and tire assembly.

Signal conductor leads 54 and 55 are electrically connected to the tire flange and ceramic ring, respectively. Signals carried thereby are passed through the mercury slipring 47 to the static conductor leads 56 and 57.

The aforedescribed mechanical elements of the invention are electrically interconnected in the manner represented by the signal schematic of FIG. 7. Along the route of web W, the traverse carriages 11 and 12 are shown to include sensors for web moisture content, M; web basis weight, B and web caliper C. Also shown in connection with the carriage 12, is a cross-direction position transducer 15. Each of these signal generators transmit the variable quality analog signals proportional to the respective conditions to an analog/digital converter 100 which produces a corresponding succession of digital values. In signal form, these corresponding digital values are transmitted from the converter to a data base computer 110 and stored with corresponding elapsed time values.

Further along the route of web W are the transducer wheels 30, 31 and 32. Wheel 30 is connected as the acoustic signal generator whereas wheels 31 and 32 are acoustic receivers. Wheel 31 is displaced a known distance along the web traveling direction (MD) from the wheel 30. Wheel 32 is displaced a known distance transversely of the web traveling direction (CD) from the wheel 30. These known distances are included with the computer 110 data base.

The electronic components of the invention include a pulse generator 120 which releases a low frequency trigger pulse signal to a high frequency sine function generator 130. For example, pulse generator 120 discharges a trigger pulse at the relatively slow rate of 1000 H. This 1000 H trigger pulse starts the 50 KH function generation which stops after the transmission of one 50 KH cycle. This intermittently emitted 50 KH signal is power amplified by element 140 to provide a 300 V, for example, peak pulse voltage at the amplifier output terminal 142. From amplifier output terminal 142, the signal is divided with a first component directed to the transducer wheel 30 and a second component directed to a programmable digitizer 160.

Transducer signals respective to the sonic receiver wheels 31 and 32 are conducted to a differential amplifier/filter 150. The filter function of the amplifier 150 limits the signals to be amplified to a narrow frequency bandwidth centered at 50 KH, for example. The filtered and amplified signal product is conducted to an appropriate signal channel of programmable digitizer 160.

The 50 KH reference frequency is the selected product of a particular embodiment of the invention and is not a limiting characteristic. In this example, the frequency was selected as follows. Relative to the graph of FIG. 8, what is seen is a passive power/frequency distribution spectrum for a particular sonic receiving transducer 31 or 32 when driven by a papermachine web at a known surface velocity. In other words, the FIG. 8 graph represents the background signal noise coming from transducers 31 or 32 without sonic stimulation from the sonic transmitter 30. Between 10 and 15 KH, the passive noise emissions are synergistic. This is the natural frequency of the system. It will also be noted that the signal amplitude begins to grow at a substantially linear rate as frequency increases beyond 50 KH. Obviously, therefore, for this particular profile, 50 KH is the frequency most distant from the 10-20 KH natural frequency band and simultaneously is accompanied by the lowest voltage amplitude.

The desired data signals transmitted from the sonic receiving transducers 31 or 32 will be the respective transducer piezoelectric response to a sonic stimulation from transducer 30 at the reference frequency. In a noiseless system, the two signals would be identical except for a "time-of-flight" delay due to transmission velocity differences through the web. The instrument objective is to precisely quantify the magnitude of this "time-of-flight."

In a real system, however, the desired data signals are immersed in a flood of noise signals thereby obscuring the exact signal pulse which signifies the time-of-flight interval. Nevertheless, the desired data signals influence the total signal, desired data plus noise. Consequently, the total signal is cross-correlated with the reference signal by the function $$R_{xy}(\tau) = \frac{lim}{T \to \infty} \frac{1}{T} \int_o^T x(t)\, y(t + \tau)\, dt$$

where:

x(t) is the reference signal at the reference frequency
y(t+τ) is the total signal Application of this cross-correlation function is a special case of probability where the total amplified signal y(t+τ) received by the programmable digitizer 160 from the respective transducers 31 and 32 is compared by a "fast Fourier transform" analysis to the reference signal x(t) received from the function generator 130.

The mechanics of such a comparison follows the format of a "fast Fourier transform" analysis. This comparison is performed by the data processing and computational units of the invention represented by FIG. 7. The process mechanics of the comparison is explained as follows with reference to FIGS. 9 through 15.

Figure 9:
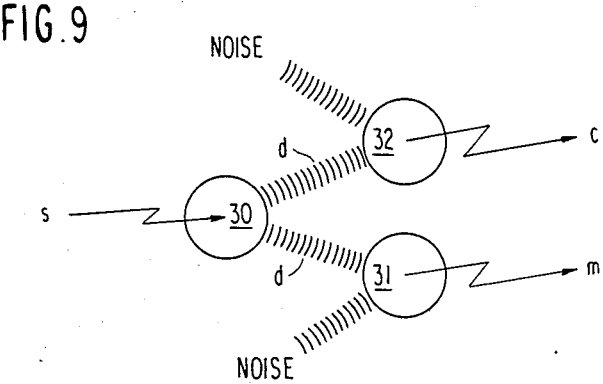
FIG. 9 schematically represents the sonic signal transmission, receipt and response relationships between the three transducer wheels of the present invention.

Transducer wheel 30 of FIG. 9 is represented as receiving a distinctive electrical stimulation signal s. This signal s is the same as that emitted at the amplifier output terminal 142 and is also the x(t) parameter of the cross-correlation function. Responsive to the stimulation of electrical signal s, transducer 30 emits sonic signals d at the same frequency as s: predominately through the web mass but also through the frame structure and atmosphere. These sonic signals d are received as stimuli by the transducer wheels 31 and 32 which are also being stimulated by other sonic sources represented collectively in FIG. 9 as noise.

Responsive to the sonic signals, d plus noise, transducers 31 and 32 emit total electrical signals c and m, respectively. These are the signals represented by FIG. 7 as received by amplifier/filter 150. Signals c and m are also the parameter $y(t+\tau)$ of the cross-correlation function.

Further explanation will delete references to signal c since both signals, c and m, are processed identically relative to stimulation signal s.

Figure 10:
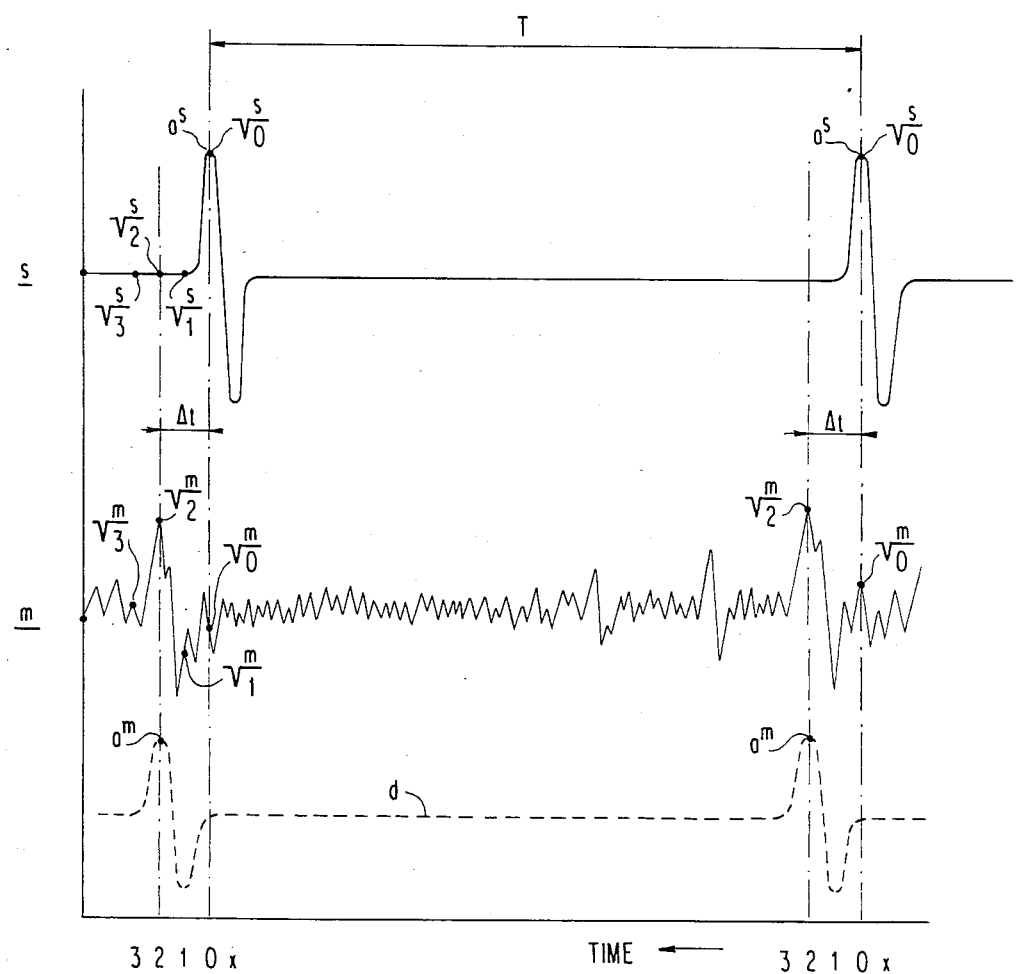
FIG. 10 is a composite signal graph illustrating representative stimulation and response signals.

Advancing the present explanation to the composite graph of FIG. 10, stimulation signal s is represented as an intermittent pulse: a single 50 KH cycle occurring at 1000 H with a peak voltage value of $a^s$ occurring at time $t_o$. Superimposed on the same time abscissa is the total response signal m and the electrical correspondent of sonic signal d as a constituent portion of total signal m. Note is given to the fact that sonic signal d has the same frequency as stimulation signal s but with a pulse apex at voltage value $a^m$. The absolute value of voltage $a^m$ is of no consequence but the time of occurrence relative to the occurrence moment of $a^s$, i.e. $\Delta t$, the process objective From superficial observation of FIG. 10, it is seen that although signal wave m is far more complex than wave d, there is an average frequency correlation between the two. To find the most probable time delay $\Delta t$ from coincidence between signals s and m, voltage data is taken from both signals over a predetermined time span T: arbitrarily selected for this example as being the same as the stimulation pulse frequency. This time span T is then divided into a number of subdivision increments $t_o, t_1, t_2, t_3 \ldots t_x$. Normally, the number of such time increments will be an exponential value of 2 i.e. $2^{10}=1024$ increments.

For each of these time increments $t_o, t_1$ etc., the momentary voltage value of each signal s and m is measured, digitialized by the converter 100. The digital values are memory stored with the computer 110 data base in series sequence corresponding to the respective time increment. Relative to the graph of FIG. 10 and the table of FIG. 11, it is seen that the initial voltage value of signal s is $$\sqrt[s]{o}.$$

This value is memory stored in the columnar order of FIG. 11 where where the voltage value $$\sqrt[s]{o}$$

is shown under the s column and $t_o$ row. Simultaneously, the initial value of signal m, $$\sqrt[m]{o},$$

is measured, digitized and stored under column m, row $t_o$.

Sequentially, signal voltage values $$\sqrt[s]{1}, \text{ and } \sqrt[m]{1}$$

are measured, converted and stored as corresponding to signals s and m, respectively, and to time increment $t_1$.

This process is repeated through time increment $t_x$ or until the end of the predetermined time span T.

These memory stored voltage values are next processed by obtaining the product of the s and m signal values respective to each time increment. In other words, for the moment $t_o$, the values $$\sqrt[s]{o} \text{ and } \sqrt[m]{o}$$

are multiplied to find the product $$P_{t0}^0.$$

Similarly, the values $$\sqrt[s]{1} \text{ and } \sqrt[m]{1}$$

are multiplied to find the product $$P_{t1}^0.$$

When all of the voltage values of corresponding time moments are expanded to respective products, these products are added to find the total product $$\Sigma P_{t_o}^{0-x}.$$

This total product $$\Sigma P_{t_o}^{0-x}$$

becomes a single data point, $\Sigma P_{t_o}$, on the cross-correlation curve of FIG. 14 at the originating time abscissa $t_o$.

To obtain the second point on the FIG. 14 cross-correlation curve, $\Sigma P_{t1}$, the m signal column data is indexed by one time increment relative to the s signal data. This concept is illustrated by FIG. 12 which shows the $$\sqrt[s]{o}$$

value combined with the $$\sqrt[m]{1}$$

value for the product

Correspondingly, the $$P^0_{t1}.$$

value respective to the s signal at time $t_1$ is multiplied by the $$\sqrt[s]{1}$$

value respective to the m signal at time $t_2$. The sum of all such indexed data, $$\sqrt[m]{2}$$

$$\Sigma P^{o \rightarrow x}_{t1},$$

becomes the second cross-correlation point $\Sigma P_{t1}$.

FIG. 13 illustrates a third example of the foregoing indexing process whereby $$\sqrt[s]{o}$$

is multiplied by the m signal value of $$\sqrt[m]{2}$$

from time increment $t_2$ for the product $$P^0_{t2}.$$

The sum of the FIG. 10 indexed products $$\Sigma P^{o \rightarrow x}_{t2}$$

yields the third point $\Sigma Pt_2$ on the cross-correlation curve of FIG. 14.

Described thus far is the computerized process for cross-correlating the voltage values characteristic of signal m to the values of signal s. FIG. 14 graphically represents a simplified iteration of this process. As actually applied, reference is made to FIG. 15 where the process produces a series of peaks along the declining slope of reference line R. The first departure from this pattern is the peak labeled $a^m$ which falls within the window interval between time moments $w_1$ and $w_2$. These time window limits are predetermined by the rational extremes of a valid time delay for the web under scrutiny considering the physical separation of the transducer wheels 30, 31 and 32 and anticipated variations in the web characteristics having a known influence over the sonic propagation velocity in paper.

Figure 15:
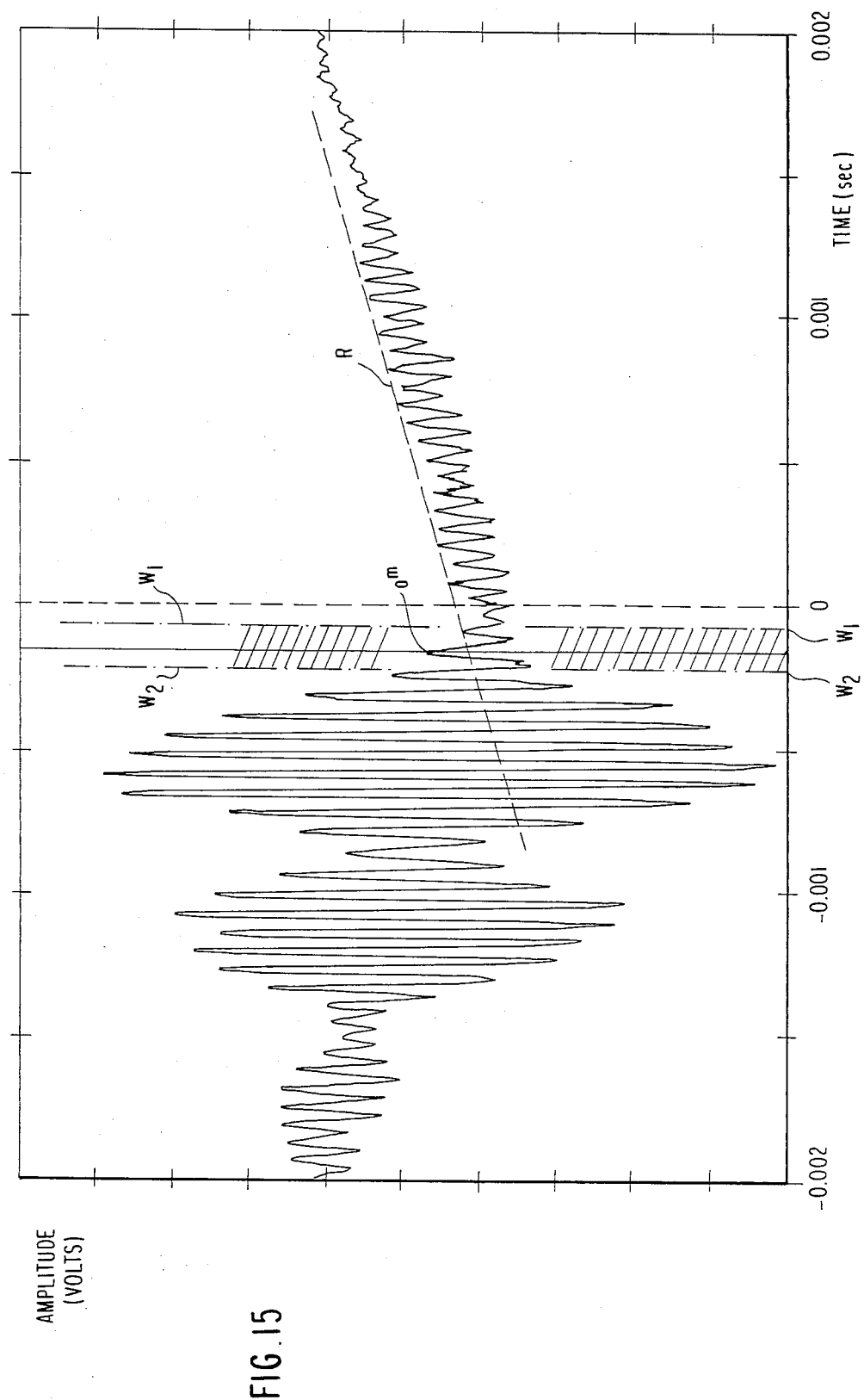
FIG. 15 is a representative actual cross-correlation plot.

In the specific example of FIG. 15, cross-correlation peak $a^m$ occurs at 0.0002 seconds after the reference moment of $t_o$. This value of 0.0002 seconds is therefore the assigned value for $\Delta t$ in determining the sonic velocity of the web in the machine direction according to the relationship $v = D/\Delta t$.

The sonic velocity of the web is combined with the moisture, basis weight and caliper characteristics to determine the strength and modulus properties of the web.

Although there are numerous other and stronger cross-correlation peaks to follow that of $a^m$, these peaks are rationally excluded from consideration as outside the predetermined time window. Such irrational peaks are the products of echoes, harmonics and other transmission media.

Having fully described our invention,

We claim:

1. An improved instrument for measuring the propagation velocity of sound within a traveling papermachine web, said improved instrument comprising at least two independently rotating transducer wheels driven by contact with one surface side of said web, each of said transducer wheels having a flanged axle with oppositely protruding bearing spindles, said spindles being confined for rotation within vibration isolated bearing means, acoustically conductive tire means concentrically surrounding said axle flange and secured thereto by an independent radial structural link, said structural link being isolated from said axle flange and said tire means by sound attenuation means and full circle piezoelectric transducer means intimately bedded with said tire means for transmitting or receiving a sonic signal through said web.

2. An instrument as described by claim 1 further comprising an idler wheel respective to each transducer wheel rotatively driven by the other surface side of said web for nipping said web into intimate contact with the perimeter of said tire means.

3. An instrument as described by claim 1 wherein said transducer wheels and idler wheels are structurally supported by respective frame means, said idler wheel frame means being selectively displacable to remove said idler wheels from the proximity of said web.

4. An instrument as described by claim 3 wherein said idler wheel frame means is pivotally connected to said transducer wheel frame means for rotation about an axis parallel with an edge of said web.

5. A method of measuring the propagation velocity of sound within a traveling papermachine web comprising the steps of:

intermittently generating a distinctive electrical reference signal;

transmitting a first component of said reference signal, to a first, rotationally independent piezoelectric transducer in continuous rolling contact with a surface of said web to stimulate the transmission a responsive sonic signal through said web;

receiving said sonic signal by a second, rotationally independent, piezoelectric transducer in continuous rolling contact with said web surface for generation of a responsive electrical signal;

transmitting said responsive electrical signals emitted by said second transducer to digital conversion means for converting a variable quality of said responsive signal to a succession of digital values corresponding to a succession of time intervals;

transmitting a second component of said reference signal to said digital conversion means for converting a variable quality of said reference signal to a succession of digital values corresponding to said succession of time intervals;

cross-correlating the digital values of said responsive and reference signals over a finite multiplicity of said time intervals;

from a physical separation distance between said first and second transducers and anticipated variations in the characteristics of said web, determining a time window between a rational range of maximum and minimum time delays for propagation of said sonic signal through said web between said first and second transducers;

selecting as a specific sonic wave propagation interval through said web between said first and second transducers, that time lapse delineated by that moment in time whereat the greatest probability of cross-correlated synchronization between said reference and response signals occurs within said time window; and, determining the sonic velocity within said web from said transducer physical separation distance and said specific sonic wave propagation interval.

* * * * *